(12) United States Patent
Kouda et al.

(10) Patent No.: US 8,408,040 B2
(45) Date of Patent: Apr. 2, 2013

(54) METHOD OF CALIBRATING PRESSURE MEASUREMENT UNIT

(75) Inventors: Masaaki Kouda, Tokyo (JP); Atsushi Karakama, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 370 days.

(21) Appl. No.: 12/745,995

(22) PCT Filed: Nov. 18, 2008

(86) PCT No.: PCT/JP2008/070919
§ 371 (c)(1),
(2), (4) Date: Jul. 1, 2010

(87) PCT Pub. No.: WO2009/072390
PCT Pub. Date: Jun. 11, 2009

(65) Prior Publication Data
US 2010/0275673 A1    Nov. 4, 2010

(30) Foreign Application Priority Data

Dec. 6, 2007    (JP) ................................ 2007-315374

(51) Int. Cl.
*G01L 27/00* (2006.01)
(52) U.S. Cl. ........................................... 73/1.69
(58) Field of Classification Search .............. 73/1.69, 73/1.71, 1.72
See application file for complete search history.

(56) References Cited

U.S. PATENT DOCUMENTS

| | | | |
|---|---|---|---|
| 4,342,218 A | 8/1982 | Fox | |
| 5,722,399 A | 3/1998 | Chevallet et al. | |
| 7,748,275 B2 | 7/2010 | Kouda et al. | |
| 2002/0095973 A1 | 7/2002 | Cole | |
| 2009/0071258 A1 | 3/2009 | Kouda et al. | |
| 2010/0275673 A1* | 11/2010 | Kouda et al. | 73/1.57 |

FOREIGN PATENT DOCUMENTS

| | | | |
|---|---|---|---|
| JP | 8-117332 | | 5/1996 |
| JP | 9-24026 | | 1/1997 |
| JP | 2010125131 A | * | 6/2010 |
| WO | 2007/123156 | | 11/2007 |

OTHER PUBLICATIONS

Prismaflex (Operator's Manual), Gambro Lundia AB, , pp. 193-199.

* cited by examiner

*Primary Examiner* — Hezron E Williams
*Assistant Examiner* — Nashmiya Fayyaz
(74) *Attorney, Agent, or Firm* — Greenblum & Bernstein, P.L.C.

(57) ABSTRACT

It is an object of the present invention to provide a method of calibrating a pressure measurement unit for measuring the pressure inside an extracorporeal circuit while avoiding contact with the air, in which, even when the connection between an air chamber of the pressure measurement unit and a pressure measurement means is disengaged accidentally or intentionally after the operation of changing the pressure inside the extracorporeal circuit from the initial pressure, the pressure measurement unit can be reconnected and the pressure inside the extracorporeal circuit can be measured stably.

After closing the extracorporeal circuit in such a way that the pressure measurement unit and a pressure adjusting means are contained in the closed section, the pressure inside the liquid chamber is adjusted to a predetermined pressure using a pressure adjusting pump, and then the pressure measurement means and the air chamber of the pressure measurement unit are connected to each other.

16 Claims, 9 Drawing Sheets

METHOD OF CALIBRATING PRESSURE MEASUREMENT UNIT

TECHNICAL FIELD

The invention relates to a method of calibrating a pressure measurement unit in an extracorporeal circuit system for delivering a liquid, in particular, a body fluid or a drug solution.

BACKGROUND ART

In extracorporeal circuit therapy where blood is taken out from the body of a patient, treated outside the body using a blood treatment apparatus, and put back into the body of the patient after treatment, a pressure measurement unit is typically used for measuring a pressure inside an extracorporeal circuit.

Japanese laid-open patent publication No. 09-024026 discloses, as an example of a means for measuring a pressure inside the extracorporeal circuit in a state in which a body fluid or a drug solution is prevented from making contact with the air, a pressure measurement unit which measures a pressure inside the extracorporeal circuit via a diaphragm.

FIG. 8 is a schematic configuration diagram showing an example of the configuration of this pressure measurement unit. A pressure measurement unit 1 is arranged in an extracorporeal circuit 8, the pressure measurement unit 1 including: an air chamber 9 having an air inlet-and-outlet port 50; a liquid chamber 6 having a liquid inlet port 40 and a liquid outlet port 41; a flexible diaphragm 20 which is sandwiched between the air chamber 9 and the liquid chamber 6 to provide a partition between the air chamber 9 and the liquid chamber 6, the flexible diaphragm 20 deforming in accordance with a pressure difference between a pressure inside the air chamber 9 and a pressure inside the liquid chamber 6; and a pressure measurement means 60 which is connected to the air inlet-and-outlet port 50 of the air chamber 9 via a communicating member 51, the pressure measurement means 60 measuring the pressure inside the liquid chamber 6 on the side of the air chamber 9 via the diaphragm. Since the flexible diaphragm 20 deforms in accordance with a change in the pressure inside the liquid chamber 6 and the pressure inside the air chamber 9 and the pressure inside the liquid chamber 6 change in a manner correlating with each other, the pressure measurement unit 1 measures the pressure inside the air chamber 9 and converts the measured value, thereby measuring the pressure inside the liquid chamber 6.

However, since the pressure measurement unit 1 shown in FIG. 8 is usually a disposable product, the pressure measurement unit 1 is configured to be detachable from the expensive pressure measurement means 60. Accordingly, if the pressure measurement means 60 and the pressure measurement unit 1 are detached from each other during use, it becomes impossible to measure the pressure in the extracorporeal circuit 8, and even they are connected to each other again, the initial position of the flexible diaphragm 20 immediately after the connection is not stable, and therefore, a pressure cannot be measured within a targeted pressure measurement range.

Gambro, Prismaflex Operator's manual, pages 193-199, discloses an example of a calibration method for solving such a problem. FIG. 9 is a schematic configuration diagram explaining the calibration method. A pressure measurement unit 1 includes: an air chamber 9 having an air inlet-and-outlet port 50; a liquid chamber 6 having a liquid inlet port 40 and a liquid outlet port 41; a flexible diaphragm 20 which is sandwiched between the air chamber 9 and the liquid chamber 6 to provide a partition between the air chamber 9 and the liquid chamber 6, the flexible diaphragm 20 deforming in accordance with a pressure difference between a pressure inside the air chamber 9 and a pressure inside the liquid chamber 6; and a pressure measurement means 60 which is connected to the air inlet-and-outlet port 50 of the air chamber 9 via a communicating member 51, the pressure measurement means 60 measuring the pressure inside the liquid chamber 6 on the side of the air chamber 9 via the flexible diaphragm 20. The communicating member 51 is configured to be detachable by a connection means 55. As shown in FIG. 9, a related art calibration system for the pressure measurement unit 1 includes the pressure measurement unit 1 arranged in an extracorporeal circuit 8; closing means 82 and 83 for closing the extracorporeal circuit 8 which are arranged on the upstream of the liquid inlet port 40 and on the downstream of the liquid outlet port 41, respectively; a sample port 84 which is arranged between the two closing means 82 and 83; and a syringe 85 which can be coupled with the sample port 84. Note that, in FIG. 9, components having the same functions as the components in FIG. 8 are indicated by the same reference numerals as those in FIG. 8.

In the pressure measurement unit 1 above, a calibration method which is carried out when the communicating member 51 in the connection means 55 is detached includes the following steps:

stopping a liquid sending means (not shown) in the extracorporeal circuit 8;

closing the liquid chamber 6 using the closing means 82 and 83;

inserting the syringe 85 into the sample port 84 and extracting 1 cc of body fluid or drug solution from the extracorporeal circuit 8 or infusing 1 cc of physiological saline into the extracorporeal circuit 8;

reconnecting the connection means 55 in the communicating member 51; and opening the closing means 82 and 83.

However, in the calibration method above, in step 2, the liquid chamber 6 is closed under the pressure of the extracorporeal circuit 8 as of the time when the liquid sending means is stopped, and therefore, for example, the liquid chamber 6 is closed by the closing means 82 with the flexible diaphragm 20 being deformed toward the liquid chamber 6 when the pressure inside the extracorporeal circuit 8 is negative, while the liquid chamber 6 is closed with the flexible diaphragm 20 being deformed toward the air chamber 9 when the pressure inside the extracorporeal circuit 8 is positive. Accordingly, the position of the flexible diaphragm 20 is not constant as it changes depending on the pressure inside the extracorporeal circuit 8 as of the time when the liquid chamber 6 is closed, and if the steps of step 3 onward are performed in such a state, the position of the flexible diaphragm 20 cannot be restored to a predetermined position at the time of starting the pressure measurement. Specifically, in the situation where the position of the flexible diaphragm 20 at the time of starting the pressure measurement has been moved toward the liquid chamber 6, the capacity of the liquid chamber 6 becomes small, and thus the measurement limit for negative pressures would be reduced and the range in which the pressure can be measured correctly would be narrowed. On the other hand, in the situation where the position of the flexible diaphragm 20 has been moved toward the air chamber 9, the capacity of the air chamber 9 becomes small, and thus the measurement limit for positive pressures would be reduced and the range in which the pressure can be measured correctly would be narrowed. Accordingly, there is a possibility that, even if the steps of step 3 onward are performed, the pressure cannot be measured correctly in a predetermined pressure measurement range. In addition, the related-art method has risks such as: a risk in which the body fluid or drug solution in the extracorporeal circuit 8 might be leaked outside the extracorporeal circuit 8 when the syringe 85 is inserted into or detached from the sample port 84; and a risk in which a needle (not shown) attached to an end of the syringe 85 might be accidentally stuck into a human body when it is inserted into the sample port, which might increase the risk of infection.

DISCLOSURE OF THE INVENTION

Problems to be Solved by the Invention

In light of the above problems in the related art, it is an object of the present invention to provide an operation method of calibrating a pressure measurement unit for measuring the pressure inside an extracorporeal circuit while avoiding contact with the air, in which: even when the connection between an air chamber of the pressure measurement unit and a pressure measurement means is disengaged accidentally or intentionally after the operation of changing the pressure inside the extracorporeal circuit from an initial pressure, the pressure measurement unit can be reconnected and the pressure inside the extracorporeal circuit can be measured stably; and there is no risk of infection caused by a body fluid or a liquid fluid leaked out from the extracorporeal circuit system.

Means for Solving the Problems

After making endeavors to solve the problem above, the inventors of the present invention found that the above problem can be solved by, when the connection between the air chamber in the pressure measurement unit and the pressure measurement means is disengaged, adjusting the pressure inside the liquid chamber to, for example, the initial pressure as of the time when an air inlet-and-outlet port of the air chamber and the pressure measurement means are connected to each other, using a pressure adjusting pump or a liquid sending pump, and thereby achieved the present invention. The present invention includes the following configurations.

(1) a method of calibrating a pressure measurement unit in an extracorporeal circuit system including: the pressure measurement unit constituted from a container having an air chamber provided with an air inlet-and-outlet port, a liquid chamber provided with a liquid inlet port and a liquid outlet port, and a flexible diaphragm that provides partition between the air chamber and the liquid chamber and that deforms in accordance with a pressure difference between a pressure inside the air chamber and a pressure inside the liquid chamber; first pressure measurement means which is connected to the air inlet-and-outlet port of the container via detachable connection means; an upstream part and a downstream part of an extracorporeal circuit connected respectively to the liquid inlet port and the liquid outlet port of the liquid chamber; closing means which close the upstream part and the downstream part of the extracorporeal circuit, respectively; second pressure measurement means which measures pressure in an extracorporeal circuit section closed by the closing means; a pressure adjusting pump arranged in the extracorporeal circuit section closed by the closing means or in a branch pipe branching from the extracorporeal circuit section; and a liquid sending pump arranged in the extracorporeal circuit, the method being carried out when a connection between the first pressure measurement means and the air inlet-and-outlet port is disengaged after starting a pressure measurement for the extracorporeal circuit, wherein: the extracorporeal circuit system further has detection means and control means; the detection means detects the disengagement of the connection between the first pressure measurement means and the air inlet-and-outlet port and transmits information of the disengagement to the control means; the control means stops the liquid sending pump and closes the upstream part and the downstream part of the extracorporeal circuit using the closing means; the second pressure measurement means measures a pressure $P_t$ of the closed extracorporeal circuit section and transmits information of the pressure $P_t$ to the control means; the control means drives the pressure adjusting pump and sets the pressure $P_t$ to a predetermined pressure $P_0$, being a pressure closer to the pressure at the time of starting the pressure measurement; and, after the setting, the first pressure measurement means and the air inlet-and-outlet port are connected to each other again.

(2) A method of calibrating a pressure measurement unit in an extracorporeal circuit system including: the pressure measurement unit constituted from a container having an air chamber provided with an air inlet-and-outlet port, a liquid chamber provided with a liquid inlet port and a liquid outlet port, and a flexible diaphragm that provides a partition between the air chamber and the liquid chamber and that deforms in accordance with a pressure difference between a pressure inside the air chamber and a pressure inside the liquid chamber; pressure measurement means which is connected to the air inlet-and-outlet port of the container via detachable connection means; an upstream part and a downstream part of an extracorporeal circuit connected respectively to the liquid inlet port and the liquid outlet port of the liquid chamber; closing means which respectively close the upstream part and the downstream part of the extracorporeal circuit; a pressure adjusting pump arranged in an extracorporeal circuit section closed by the closing means or in a branch pipe branching from the extracorporeal circuit section; and a liquid sending pump arranged in the extracorporeal circuit, the method being carried out when a connection between the pressure measurement means and the air inlet-and-outlet port is disengaged after starting a pressure measurement for the extracorporeal circuit, wherein: the pressure measurement means is connectable to the closed extracorporeal circuit section; the extracorporeal circuit system further has detection means and control means; the detection means detects the disengagement of the connection between the pressure measurement means and the air inlet-and-outlet port and transmits information of the disengagement to the control means; the control means stops the liquid sending pump and closes the upstream part and the downstream part of the extracorporeal circuit using the closing means; the pressure measurement means is connected to the closed extracorporeal circuit section, measures a pressure $P_t$ of the closed extracorporeal circuit section and transmits information of the pressure $P_t$ to the control means; the control means drives the pressure adjusting pump and sets the pressure $P_t$ to a predetermined pressure $P_0$, being a pressure closer to the pressure at the time of starting the pressure measurement; and, after the setting, the connection between the pressure measurement means and the closed extracorporeal circuit section is disengaged, and the pressure measurement means and the air inlet-and-outlet port are connected to each other again.

(3) The method of calibrating the pressure measurement unit of the extracorporeal circuit system described in (1) or (2), wherein the control means automatically drives the pressure adjusting pump based on the information of the pressure $P_t$ and the pressure $P_0$, and sets the pressure $P_t$ to the pressure $P_0$.

(4) The method of calibrating the pressure measurement unit of the extracorporeal circuit system described in (1) or (2) wherein: the extracorporeal circuit system further has display means and input means; the control means displays information of the pressure $P_t$ and the pressure $P_0$, on the display means; the display means instructs an operator to input information for setting the pressure $P_t$ to the pressure $P_0$ via the input means; and the control means drives the pressure adjusting pump based on the information input via the input means so as to set the pressure $P_t$ to the pressure $P_0$.

(5) The method of calibrating the pressure measurement unit of the extracorporeal circuit system described in any one of (1) to (4), wherein: the pressure adjusting pump is arranged in the branch pipe; and a terminal end of the branch pipe is connected to a liquid supply source.

(6) The method of calibrating the pressure measurement unit of the extracorporeal circuit system described in any one of (1) to (4), wherein: the pressure adjusting pump is arranged in the branch pipe; and a terminal end of the branch pipe is open to the atmosphere.

(7) The method of calibrating the pressure measurement unit of the extracorporeal circuit system described in any one of (1) to (6), wherein: the pressure adjusting pump is arranged in the branch pipe; and the liquid sending pump has a movable housing which opens or closes the extracorporeal circuit, the liquid sending pump being arranged in the closed extracorporeal circuit section, the housing opening the extracorporeal circuit before the operation of setting the pressure $P_t$ to the pressure $P_0$.

(8) The method of calibrating the pressure measurement unit of the extracorporeal circuit system described in any one of (1) to (4), wherein the pressure adjusting pump is arranged in the extracorporeal circuit and integrated with the liquid sending pump and the closing means.

(9) The method of calibrating the pressure measurement unit of the extracorporeal circuit system described in any one of (1) to (8), wherein two or more pressure measurement units are arranged.

Advantages of the Invention

With the method of calibrating the pressure measurement unit according to the present invention, even when the connection between the air chamber in a pressure measurement unit and the pressure measurement means is disengaged accidentally or intentionally after the operation of changing the pressure inside the extracorporeal circuit from the initial pressure, the calibration of the pressure measurement unit can be carried out easily, safely and correctly, and the pressure measurement for the extracorporeal circuit can be restarted.

Figure 1:
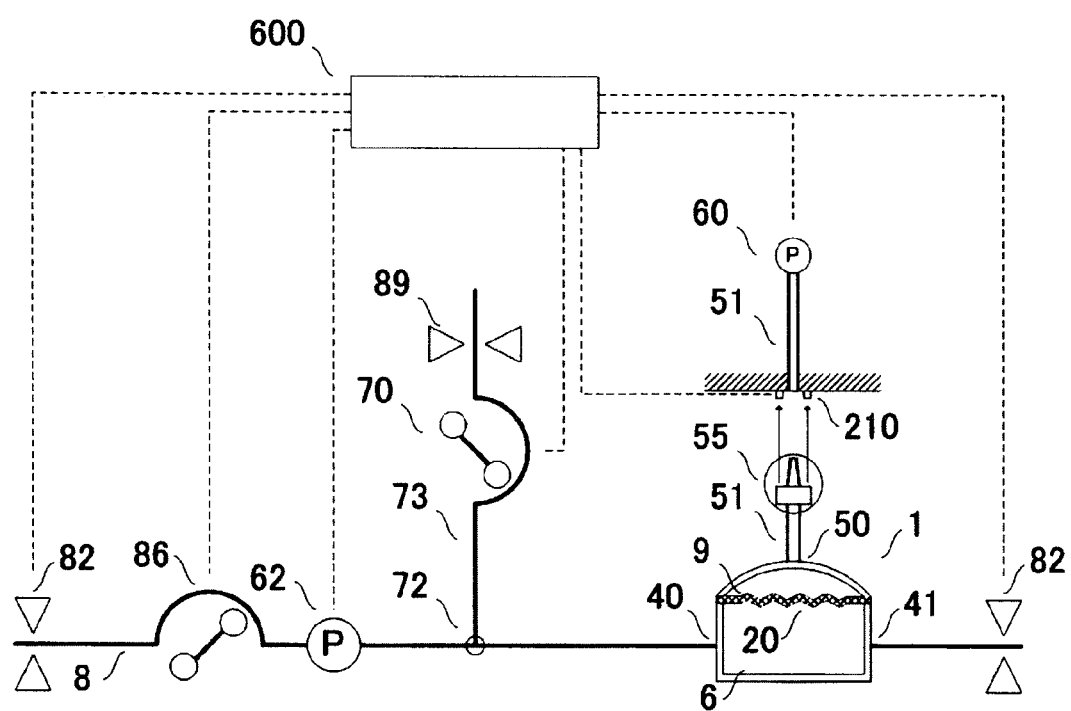
FIG. 1 is a schematic diagram showing a first embodiment for carrying out a method of calibrating a pressure measurement unit according to the present invention.

DESCRIPTION OF REFERENCE NUMERALS 1, 1': pressure measurement unit
2: drip chamber
6: liquid chamber
8: extracorporeal circuit
9: air chamber
20: flexible diaphragm
40: liquid inlet port
41: liquid outlet port
50: air inlet-and-outlet port
51: communicating member
55: first connection means (connection means)
56: second connection means
60: first pressure measurement means (pressure measurement means)
62: second pressure measurement means
70: pressure adjusting pump
72: branch point
73: branch pipe
74: second branch point
75: second branch pipe
76: liquid supply source
82: closing means
84: sample port
85: syringe
86: liquid sending means
87: blood purifier
88: movable housing
89: closing means for a branch pipe
210: detection means
240: pressure measurement unit holder
600: control means
610: display means
620: input means

BEST MODE FOR CARRYING OUT THE INVENTION

Embodiments of a method of calibrating a pressure measurement unit according to the present invention will be described below with reference to the attached drawings, but the present invention is not limited to these embodiments. The method of calibrating the pressure measurement unit according to the present invention is used when the connection between an air chamber in the pressure measurement unit and an air chamber pressure measurement means is disengaged at a connection means 55 accidentally due to a certain factor or when such a connection is disengaged intentionally for a certain reason. For example, the connection might be disengaged after a leak check or priming using the air performed before starting extracorporeal circulation treatment, or accidentally disengaged during extracorporeal circulation treatment.

First Embodiment

FIG. 1 is a schematic diagram showing an embodiment for carrying out the method of calibrating a pressure measurement unit according to the present invention.

As shown in FIG. 1, a pressure measurement unit 1 includes: a container provided with an air chamber 9 having an air inlet-and-outlet port 50, a liquid chamber 6 having a liquid inlet port 40 and a liquid outlet port 41, and a flexible diaphragm 20 which is sandwiched between the air chamber 9 and the liquid chamber 6 to provide a partition between the air chamber 9 and the liquid chamber 6, the flexible diaphragm 20 deforming in accordance with a pressure difference between a pressure inside the air chamber 9 and a pressure inside the liquid chamber 6; and a first pressure measurement means 60 which is connected to the air inlet-and-outlet port 50 of the air chamber 9 via a connection means 55, the first pressure measurement means 60 measuring the pressure inside the liquid chamber 6 on the side of the air chamber 9 via the flexible diaphragm 20.

The first embodiment for carrying out the method of calibrating the pressure measurement unit according to the present invention includes: the pressure measurement unit 1 which is arranged in an extracorporeal circuit 8 sandwiched between two closing means 82; a liquid sending means 86 for sending a body fluid or a drug solution; a second pressure measurement means 62 which measures a pressure inside the extracorporeal circuit 8; a branch point 72; a branch pipe 73 which is connected to the branch point 72; a pressure adjusting pump 70 arranged in the branch pipe 73; a detection means 210 which detects the attachment of the pressure measurement unit 1; and a control means 600 which controls the operations of the liquid sending means 86, the closing means 82 and the pressure adjusting pump 70, judges the attachment state of the pressure measurement unit 1 based on information from the detection means 210, and receives pressure information from the first pressure measurement means 60 and the second pressure measurement means 62 (FIG. 1).

The upstream and downstream of the extracorporeal circuit 8 is defined based on the direction in which a liquid flows during extracorporeal circulation. For example, the upstream of the pressure measurement unit 1 refers to the side of the liquid inlet port 40, while the downstream thereof refers to the side of the liquid outlet port 41. In the branch pipe 73 of the extracorporeal circuit 8, the upstream refers to the side closer to the extracorporeal circuit 8 while the downstream refers to the side farther from the extracorporeal circuit 8.

The pressure measurement unit 1 is arranged in the extracorporeal circuit 8 and measures a pressure inside the extracorporeal circuit 8. In the pressure measurement unit 1, a change in the pressure of the liquid chamber 6 causes the flexible diaphragm 20 to deform, and the pressure of the air chamber 9 and the pressure of the liquid chamber 6 change in such a manner correlating with each other. Accordingly, by measuring the pressure inside the air chamber 9 and converting the measured value, the pressure inside the liquid chamber 6 is measured.

The pressure measurement unit 1 is connected to the pressure measurement means 60 during use, and at this time, the initial position of the flexible diaphragm 20 is determined based on the initial pressures inside the liquid chamber 6 and the air chamber 9. The initial pressure inside the air chamber 9 is the atmospheric pressure since the air inlet-and-outlet port 50 is opened to the atmosphere. The initial pressure inside the liquid chamber 6 should be suitably selected based on a measurement range for the pressure, and the initial pressure being required to be in the range between −200 mmHg and 200 mmHg, preferably in the range between −100 mmHg and 100 mmHg, and most preferably between −50 mmHg and 50 mmHg.

In the initial state described above, the air chamber 9 of the pressure measurement unit 1 is hermetically connected to the pressure measurement means 60 by the connection means 55. Employing the pressure at this time as the initial pressure, the pressure measurement unit 1 measures the pressure inside the liquid chamber 6 via the flexible diaphragm 20.

However, during the pressure measurement, if the connection between the air chamber 9 of the pressure measurement unit 1 and the pressure measurement means 60 is disengaged at the connection means 55, the initial position of the flexible diaphragm 20 changes depending on the pressure inside the liquid chamber 6 at this time. Specifically, if the pressure inside the liquid chamber 6 is higher than the initial pressure, the position of the flexible diaphragm 20 changes toward the air chamber 9, while if the pressure inside the liquid chamber 6 is lower than the initial pressure, the position of the flexible diaphragm 20 changes toward the liquid chamber 9. Accordingly, if the connection means 55 is detached and then reconnected as is, the position of the flexible diaphragm 20 changes in accordance with the pressure inside the liquid chamber 6. If the pressure inside the liquid chamber 6 is higher than the initial pressure, the maximum pressure measurement range is reduced, while if the pressure inside the liquid chamber 6 is lower than the initial pressure, the minimum pressure measurement range is reduced, and a correct pressure measurement cannot be maintained stably within a predetermined pressure measurement range.

The following description will describe in detail, in the embodiment shown in FIG. 1, a method of calibrating the pressure measurement unit 1 which is carried out when the connection between the air inlet-and-outlet port 50 of the container on the air chamber 9 side and the first pressure measurement means 60 is disengaged and it becomes impossible to continue the pressure measurement. First, the detection means 210 detects the detachment of the pressure measurement unit 1 and transmits such information to the control means 600. The control means 600, upon the receipt of this information, stops the liquid sending means 86 and closes the extracorporeal circuit 8 using the two closing means 82. Next, the second pressure measurement means 62 measures a pressure $P_t$ of the closed section in the extracorporeal circuit 8 and transmits the information of the pressure $P_t$, to the control means 600, and the control means 600 controls, while monitoring the pressure using the second pressure measurement means 62, the pressure adjusting pump 70 so as to set the pressure inside the liquid chamber 6 to a predetermined pressure $P_0$ which is closer to the initial pressure at the time of starting the pressure measurement, thereby restoring the flexible diaphragm 20 to the position which allows for pressure measurement within a targeted pressure measurement range. Finally, by hermetically connecting the first pressure measurement means 60 and the air inlet-and-outlet port 50 of the air chamber 9 to each other using the connection means 55, it becomes possible to carry out stable pressure measurement again. The predetermined pressure $P_0$ herein refers to a pressure which causes the flexible diaphragm 20 to move to a position where the pressure measurement within the targeted pressure measurement range can be achieved. Although the initial pressure is most preferable, an allowable range of the predetermined pressure $P_0$ may be arbitrarily set based on the targeted pressure measurement range, which is preferably within +/−50 mmHg of the initial pressure, more preferably within +/−20 mmHg of the initial pressure, and most preferably within the +/−5 mmHg of the initial pressure.

A medium which transmits the information related to the pressures measured by the first pressure measurement means 60 and the second pressure measurement means 62 to the control means 600 is not particularly limited, examples of which may include, in addition to numerical information representing pressure measurements, values converted into voltages, values converted into resistances, as well as values which are obtained by converting these values into second and third media such as ASCII codes. The first pressure measurement means 60 may be any means capable of measuring the air pressure inside the air chamber 9 and measuring a pressure via a gas, and examples thereof include pressure measurements using a pressure transducer and a Bourdon-tube gauge, without being particularly limited.

Figure 2:
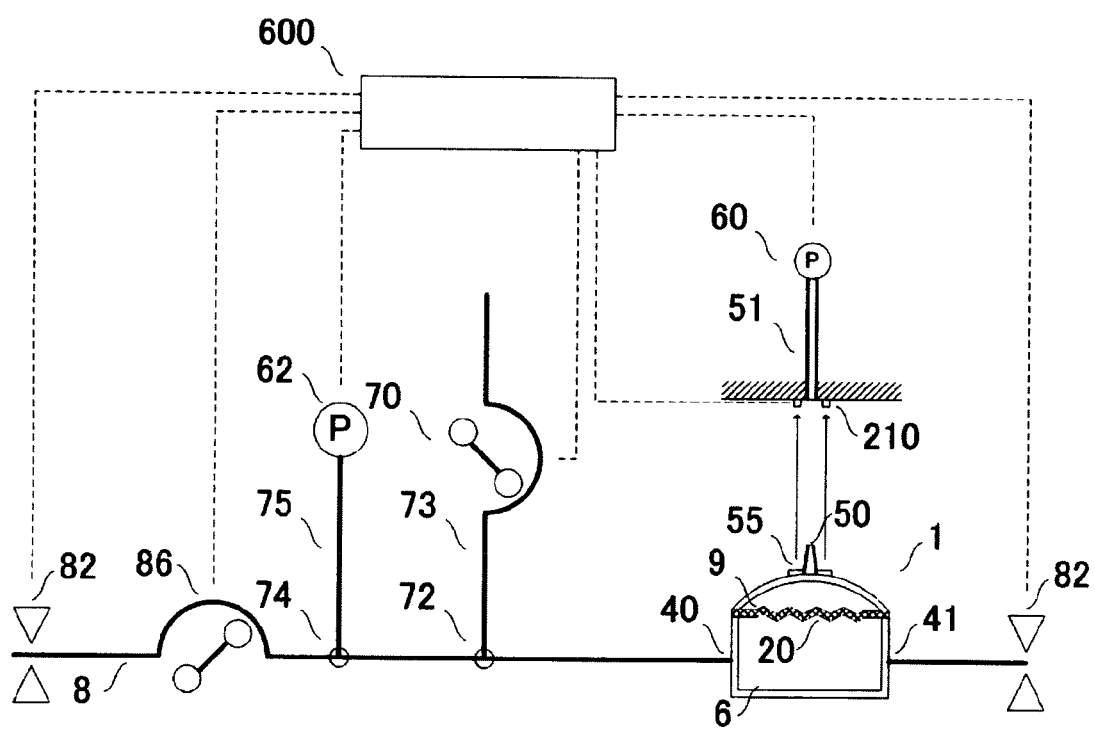
FIG. 2 is a schematic diagram showing another aspect of the first embodiment for carrying out the method of calibrating the pressure measurement unit according to the present invention.

The second pressure measurement means 62 may be any means capable of measuring the pressure inside the extracorporeal circuit 8 or inside the liquid chamber 6. For example, as shown in FIG. 1, a pressure measurement means which is directly connected to the extracorporeal circuit 8 may be employed, examples of which include: a displacement sensor which measures the amount of deformation of the extracorporeal circuit 8 deforming in accordance with the pressure inside the extracorporeal circuit 8 and converts the measured amount of deformation into a pressure; and a strain gauge which measures the amount of strain in the extracorporeal circuit 8 and converts the measured strain into a pressure. As another example, as shown in FIG. 2, a pressure measurement means which is connected to the distal end of a second branch pipe 75 branching from a second branch point 74 on the extracorporeal circuit 8, the examples of which include a pressure transducer and a Burdon-tube gauge. Furthermore, the second pressure measurement means 62 may be configured from: a pressure measurement unit having the same configurations as the pressure measurement unit 1; and a pressure measurement means, the second pressure measurement means 62 not being particularly limited.

The closing means 82 may be any closing means which can be controlled by the control means 600, examples of which include an electrically-operated valve. As examples of the electrically-operated valve, a rotary solenoid valve and a push-pull valve may be provided, but the closing means 82 is not limited thereto and may employ any means which can close and open the extracorporeal circuit 8.

Examples of the connection means 55 may include a connection using a lure connector and a coupler, as well as an insertion of a sleeve-shaped tube, but the connection means 55 may not be limited thereto and may employ any means which can hermetically connect the pressure measurement means 60 and the air inlet-and-outlet port of the air chamber 9 to each other.

In FIG. 1, the air inlet-and-outlet port 50 of the air chamber 9 and the connection means 55 are connected to each other via the communicating member 51. However, the air inlet-and-outlet port 50 of the air chamber 9 and the connection means 55 may be connected to each other without the communicating member 51 therebetween. Although the first pressure measurement means 60 is connected to the communicating member 51, the communicating member 51 may not be provided. In such a configuration, the first pressure measurement means 60 is connected detachably to the connection means 5 without the communicating member 51 therebetween.

Figure 3:
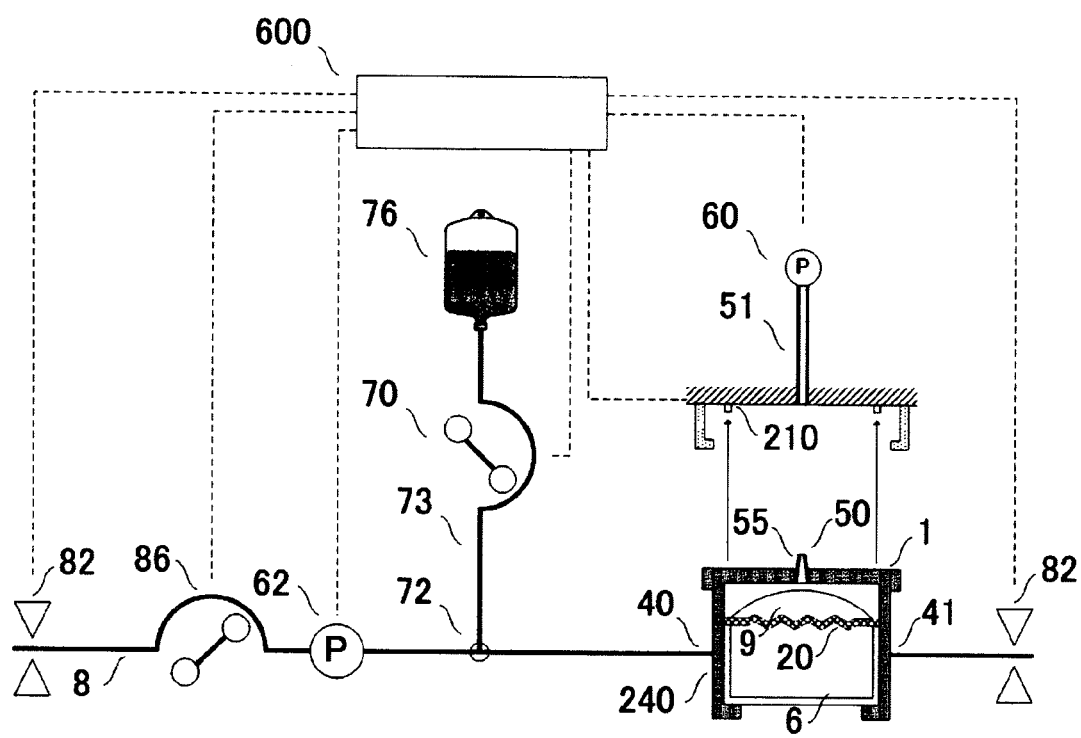
FIG. 3 is a schematic diagram showing another aspect of the first embodiment for carrying out the method of calibrating the pressure measurement unit according to the present invention.

The detection means 210 may include, for example, detection using a microswitch or magnetism. In FIG. 1, the detection means 210 is arranged so as to detect the connection of the connection means 55 which is connected to the pressure measurement unit 1 via the communicating member 51, but the detection means 210 may be alternatively configured to make contact directly with the pressure measurement unit 1 and thereby detect the attachment state thereof as shown in FIG. 2, or may further alternatively be configured to detect the connection of a pressure measurement unit holder 240 attached to the pressure measurement unit 1 and thereby indirectly detect the attachment state of the connection means 55 as shown in FIG. 3. In short, the detection means 210 may be any means which can detect the connection state of the connection means 55 and is not particularly limited. Examples of the means for transmitting the attachment state detected by the detection means 210 to the control means 600 may include a method of transmitting the ON/OFF states of the microswitch as an electric signal to the control means 600 and a method of sending information representing changes in a magnetic field to the control means 600, but any information which enables the judgment of attachment state can be employed without being particularly limited.

In addition, although one pressure measurement unit 1 is provided between the two closing means 82 in FIGS. 1, 2 and 3, the provision of two or more pressure measurement units 1 would not degrade the above-mentioned effects of the present invention, and thus the number of pressure measurement units 1 is not particularly limited.

The pressure adjusting pump 70 is a pump which can be controlled by the control means 600 so as to send a gas or a liquid, and may employ any pump which can adjust the pressure inside the extracorporeal circuit 8 and the pressure inside the liquid chamber 6. For example, a centrifugal pump and an axial flow pump may be employed. The centrifugal pump and the axial flow pump do not have a function for stopping the delivery of the liquid/gas when the pump is stopped. Accordingly, it is necessary to provide, in the branch pipe 73, a closing means 89 for the branch pipe on the downstream of the pressure adjusting pump 70 as shown in FIG. 1 or a closing means 89 for the branch pipe on the upstream of the pressure adjusting pump 70.

However, if a tube pump which can send a gas or a liquid and which has a function for stopping the delivery of the liquid/gas when the pump is stopped is used, the closing means 89 for the branch pipe and the pressure adjusting pump 70 can be integrated as shown in FIG. 2. Examples of such a pump may include a rotary tube pump. The rotary tube pump includes: an elastic tube which defines a liquid sending path; and a rotary body provided with a plurality of rollers on the outer circumference thereof, in which the rotation of the rotary body causes the plurality of rollers to squeeze the tube, thereby sending out the liquid. In the rotary tube pump, the tube is set so as to extend in an arcuate shape on the rollers of the rotary tube pump, and since the plurality of rollers constantly close the tube, the pressure inside the liquid chamber does not change while the pump is not being operated. The center of the arc of the tube coincides with the center of the rotary body, and the plurality of rollers revolves and rotates and thereby squeezes the tube to send out the liquid.

The object sent by the pressure adjusting pump 70 may either be a gas or a liquid. When a gas is to be sent, the distal end of the branch pipe 73 may be open to the atmosphere as shown in FIGS. 1 and 2. In this configuration, the distal end of the branch pipe 73 may be preferably provided with a membrane filter (not shown) in order to avoid direct contact with the outside air and to maintain an aseptic condition in the extracorporeal circuit 8. When a liquid is to be sent, the distal end of the branch pipe 73 may be connected to a liquid supply source 76 as shown in FIG. 3.

Examples of the gas to be sent may include the air, and examples of the liquid to be sent may include physiological saline and anticoagulant agents, but the gas and the liquid are not particularly limited thereto. The liquid supply source 76 may be any source which can store liquid to be supplied to the extracorporeal circuit 8 or to the liquid chamber 6, examples of which may include a soft container such as an infusion solution bag as well as a rigid container made of a rigid plastic, without being particularly limited thereto.

Figure 4:
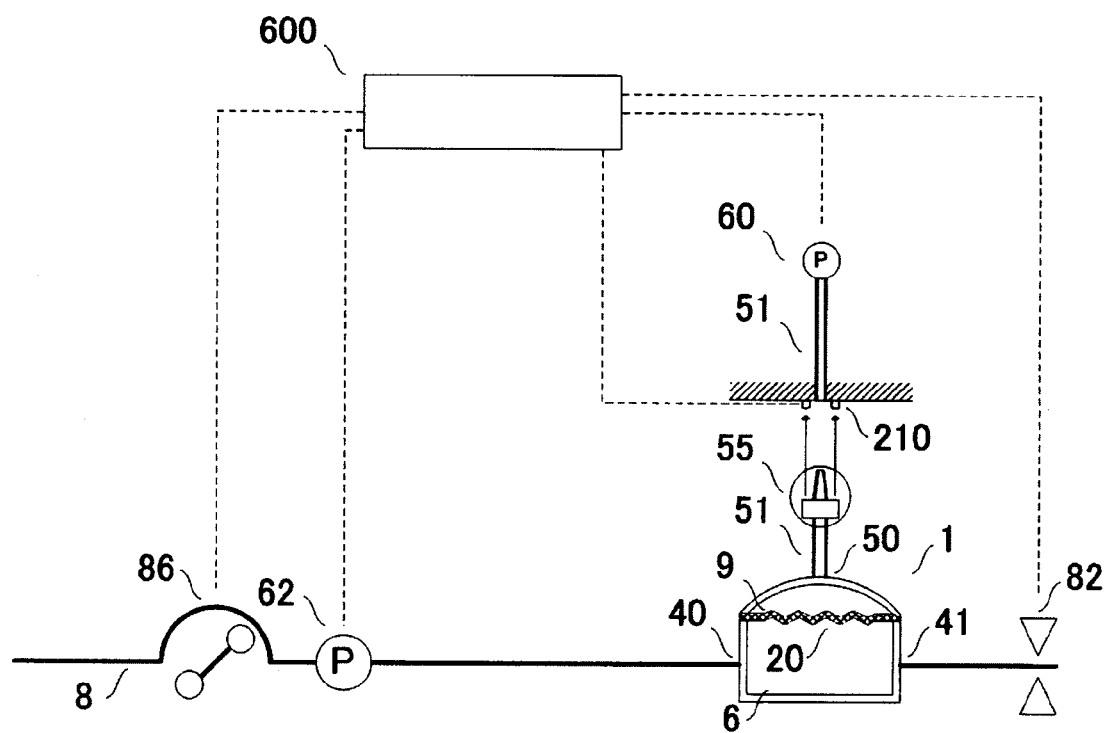
FIG. 4 is a schematic diagram showing another aspect of the first embodiment for carrying out the method of calibrating the pressure measurement unit according to the present invention.

The liquid sending means 86 may employ any means which can be controlled by the control means 600 and which send a body fluid or a drug solution in the extracorporeal circuit 8. For example, a centrifugal pump and an axial flow pump may be employed. The centrifugal pump and the axial flow pump do not have a function for stopping the delivery of the liquid when the pump is stopped. Accordingly, it is necessary to provide two closing means 82 in the extracorporeal circuit 8 as shown in FIG. 1. However, if a tube pump which can send a liquid and which has the function of stopping the delivery of the liquid when the pump is stopped is used, the closing means 82 in the extracorporeal circuit 8 and the liquid sending means 86 can be integrated as shown in FIG. 4. Examples of such a pump may include a rotary tube pump. The rotary tube pump includes: an elastic tube which defines a liquid sending path; and a rotary body provided with a plurality of rollers on the outer circumference thereof, in which the rotation of the rotary body causes the plurality of rollers to squeeze the tube, thereby sending out the liquid. In the rotary tube pump, the tube is set so as to extend in an arcuate shape on the rollers of the rotary rube pump, and since the plurality of rollers constantly close the tube, the pressure inside the liquid chamber does not change while the pump is not being operated. The center of the arc of the tube coincides with the center of the rotary body, and the plurality of rollers revolves and rotates and thereby squeezes the tube to send out the liquid. In addition, when the liquid sending means 86 and the closing means 82 in the extracorporeal circuit 8 are integrated, the pressure inside the closed extracorporeal circuit 8 can be adjusted using the liquid sending means 86, which eliminates the need for the pressure adjusting pump 70 and the branch pipe 73.

In the process in which the above-described second pressure measurement means 62 measures the pressure $P_t$ of the closed section in the extracorporeal circuit 8 and transmits the information of the pressure $P_t$ to the control means 600, and the control means 600 controls the pressure inside the liquid chamber 6, while monitoring the pressure with the second pressure measurement means 62, so as to be set to a predetermined pressure $P_0$ using the pressure adjusting pump 70, a calibration can be carried out more easily than in the process in which the pressure adjusting pump 70 is driven automatically based on the information related to $P_t$ and $P_0$ so as to set the pressure $P_t$ to the pressure $P_0$.

Figure 5:
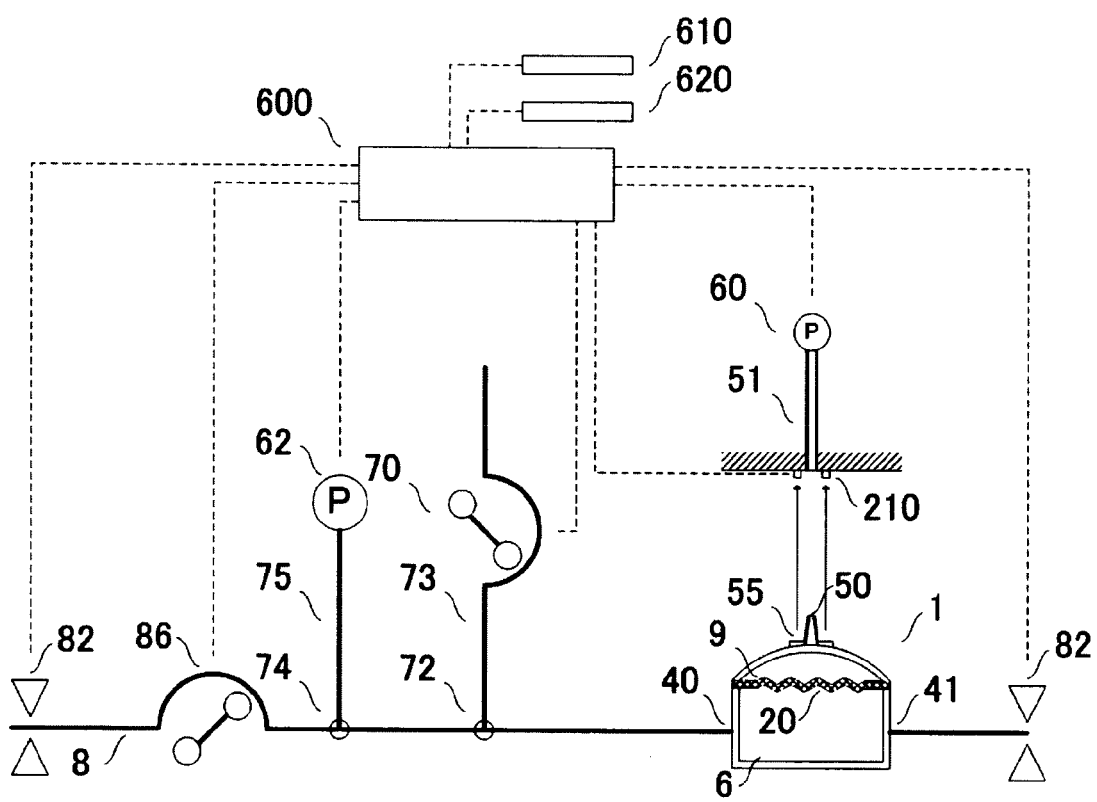
FIG. 5 is a schematic diagram showing the first embodiment for carrying out the method of calibrating the pressure measurement unit according to the present invention.

In the above process for controlling pressure, when the pressure adjusting pump 70 is driven so as to discharge the liquid from the extracorporeal circuit 8, the liquid in the extracorporeal circuit 8 might leak out. In order to prevent such leakage, the second branch pipe 75 may be provided with a membrane filter (not shown); however, such a membrane filter might be wetted. Then, as shown in FIG. 5, the control means 600 displays the pressure $P_t$ and the pressure $P_0$ on a display means 610, and the display means 610 instructs an operator to operate the pressure adjusting pump 70 using an input means 620, thereby allowing the operator to adjust the pressure inside the extracorporeal circuit 8 while monitoring the position of the liquid inside the extracorporeal circuit 8, which prevents the risk of liquid leakage from the extracorporeal circuit 8 and the risk of wetting of the membrane filter.

The display means 610 may be any means which can display the pressure $P_t$ and the pressure $P_0$, as well as the instruction for a calibration method. Examples of the display means include: a display method for displaying all such information at a time on a monitor such as a liquid crystal display and a cathode ray tube; and a display method in which only pressure information is displayed on a display such as the above-mentioned monitor or a LED display and the operation method is displayed on another display such as an electronic signboard using LED, etc.

The input means 620 may be any means which enables the control means 600 to recognize the content of input given by the operator. Examples of the input means 620 may include switches arranged on a touch panel display and switches having contacts such as button switches and lever switches, without being particularly limited thereto.

(Material)

The material of the container on the liquid chamber side and the container on the air chamber side may either be soft or rigid. However, if the shapes of the liquid chamber 6 and the air chamber 9 are changed due to environmental factors such as liquid temperature and air temperature, as well as external forces which deform the liquid chamber 6 and the air chamber 9, it would become difficult to correctly measure the pressure inside the extracorporeal circuit 8. Accordingly, the materials of the container on the liquid chamber side and the container on the air chamber side are preferably rigid, and more preferably biocompatible since the materials directly or indirectly make contact with body fluids of patients. Examples of such materials may include vinyl chloride, polycarbonate, polypropylene, polyethylene and polyurethane, and any of them may be used properly. Manufacturing method of the container is not limited, examples of which may include, injection molding, blow molding and cutting.

Regarding the material of the flexible diaphragm 20 that is deformed by pressure, if it is rigid, the amount of deformation caused by pressure would be small and it would become difficult to correctly measure the pressure inside the liquid flow path 8, and thus it is preferable to employ a soft material which flexibly deforms in accordance with pressure. In addition, it is more preferable that the material is biocompatible since it directly or indirectly makes contact with the body fluids of patients. For example, polyvinyl chloride, silicone resins, styrene thermoplastic elastomers, styrene thermoplastic elastomer compounds may be employed, and any of them may be used properly.

The materials of the extracorporeal circuit 8, the branch pipe 73, the second branch pipe 75 and the communicating member 51 may be any of synthetic resin, metal, glass and the like, but synthetic resin, in particular, thermoplastic resin is preferable in terms of production cost, processability and usability. Examples of the thermoplastic resin may include, polyolefin resin, polyamide resin, polyester resin, polyurethane resin, fluorine resin, silicone resin, ABS (acrylonitrile butadiene styrene) resin, polyvinyl chloride, polycarbonate, polystyrene, polyacrylate and polyacetal, and any of them can be used properly. Among these materials, soft materials are preferable since they have bending strength and resistance to cracking and exhibit excellent flexibility in use, and flexible polyvinyl chloride is particularly preferable in terms of its ease of fabrication.

(Bonding Method)

Bonding methods for the container on the liquid chamber side, the container on the air chamber side and the extracorporeal circuit 8 are not particularly limited. However, in general, examples of bonding for synthetic resin include hot melt bonding and adhesion, examples of hot melt bonding including high-frequency welding, induction welding, ultrasonic welding, friction welding, spin welding, hot plate welding and hot wire welding, examples of adhesives including cyanoacrylate adhesives, epoxy adhesives, polyurethane adhesives, synthetic rubber adhesives, ultraviolet cure adhesives, polyacrylate adhesives, modified acrylic adhesive and hot melt adhesives.

Bonding methods for bonding the flexible diaphragm 20, the container on the air chamber side and the container on the liquid chamber side are not particularly limited. In general, however, a mechanical sealing in which a rigid material holds a soft material, thereby providing sealing therebetween, as well as the hot melt bonding and adhesion described above, may be employed for bonding a soft material and a rigid material.

Although the pressure measurement unit 1 described above may be used as is after the molding and bonding, it is used after sterilization especially in a medical use such as extracorporeal circulation treatment. The sterilization method may be selected in accordance with sterilization methods for normal medical devices, and the pressure measurement unit 1 may be sterilized by drug solutions, gasses, radiation rays, high-pressure steam, heating and the like.

(Shape)

In FIG. 1, the cross-sectional shape of the liquid chamber 6 is rectangular. Although no particular problem can be seen in employing a dome-shaped cross section, a polygonal cross section and a trapezoidal cross section, the rectangular cross section is preferable since it is not likely to allow the liquid accumulated therein, and the rectangular cross section with its four corners rounded is most preferable.

The cross-sectional shape of the air chamber 9 is a dome shape. Although no particular problem can be seen in employing a rectangular shape and a polygon shape, the dome shape is most preferable since it allows the flexible diaphragm 20 to deform easily.

Also, no particular problem can be seen in forming the front shape of the liquid chamber 6 (the shape as seen from the direction orthogonal to the plane of the flexible diaphragm 20) in a circular shape, an ellipsoidal shape and a polygon shape, and it does not have to be point symmetric. However, the circular shape is most preferable since it forms a smooth flow of liquid.

In addition, no particular problem can be seen as well in forming the front shape of the air chamber 9 (the shape as seen from the direction orthogonal to the plane of the flexible diaphragm 20) in a circular shape, an ellipsoidal shape and a polygon shape. However, the circular shape is most preferable since it allows the air chamber 9 to easily follow the deformation of the flexible diaphragm 20 and to be molded easily.

The shapes of the liquid inlet port 40 and the liquid outlet port 41 are not particularly limited, but the liquid inlet port 40 and the liquid outlet port 41 are preferably formed in shapes that match with the extracorporeal circuit 8 to which they are connected. In blood purification therapy, an extracorporeal circuit 8 having the internal diameter of 2 mm to 5 mm is typically selected. The cross-sectional shape of the extracorporeal circuit 8 may be, in addition to the circular shape, an ellipsoidal shape and non-circular shapes such as a rectangular shape and a hexagon shape, and the shapes of the liquid inlet port 40 and the liquid outlet port 41 may be selected in accordance with the cross-sectional shape of the extracorporeal circuit 8.

The shape of the air inlet-and-outlet port 50 of the air chamber 9 is not particularly limited, but the air inlet-and-outlet port 50 is preferably formed in a shape that matches with the connection means 55 or the communicating member 51 to which it is connected. The cross-sectional shapes of the connection means 55 and the communicating member 51 may be, in addition to the circular shape, an ellipsoidal shape and non-circular shapes such as a rectangular shape and a hexagon shape, and the shapes of the air inlet-and-outlet port 50 may be selected in accordance with the cross-sectional shape of the connection means 55 or the communicating member 51.

In FIG. 1, the cross-sectional shape of the flexible diaphragm 20 is a waveform. However, any shape which allows pressure to be measured via the flexible diaphragm 20 may be employed, and no problem can be seen in employing other shapes such as a sine curve shape and a flat plate shape. The cross-sectional shape of the flexible diaphragm 20 may be preferably point symmetric around the center thereof, in terms of the ease of molding and fabrication.

In FIG. 1, although the positions of the liquid inlet port 40 and the liquid outlet port 41 are linearly arranged, the positions thereof would not affect the effects of the present invention and thus the positions are not particularly limited.

The air inlet-and-outlet port 50 of the air chamber 9 is arranged at a position most distant from the flexible diaphragm 20 in the air chamber 9, and the position thereof would not affect the effects of the present invention, and thus the position is not particularly limited.

(Size)

If the size of the liquid chamber 6 is too large, the priming volume becomes large. On the other hand, if the size is too small, the flexible diaphragm 20 cannot be deformed so much when the pressure of the extracorporeal circuit 8 becomes negative, and therefore a problem would arise where a pressure measurement range would be small. Accordingly, the size in volume of the liquid chamber 6 is preferably around 1 $mm^3$ to 10 $mm^3$, more preferably around 1 $mm^3$ to 5 $mm^3$, and most preferably around 1 $mm^3$ to 3 $mm^3$.

If the size of the air chamber 9 is too large, the diaphragm 20 is greatly deformed toward the liquid chamber 6 while the pressure is negative, and a pressure measurement range in the negative pressure side becomes small. On the other hand, if the size is too small, the flexible diaphragm 20 is likely to contact with the inner wall of the air chamber 9 while the pressure is positive, and thus a pressure measurement range on the positive pressure side becomes small. Accordingly, the size in volume of the air chamber 9 is preferably around 0.2 $mm^3$ to 1.0 $mm^3$, and more preferably around 0.3 $mm^3$ to 0.8 $mm^3$.

If the volume of the communicating member 51 is too large, the volume in combination with the volume of the air chamber 9 becomes accordingly large, and the flexible diaphragm 20 is greatly deformed while the pressure is negative, and thus the pressure measurement range on the negative pressure side becomes small.

If the volume of the communicating member 51 is too small, the distance between the air inlet-and-outlet port 50 and the pressure measurement means 60 becomes small, and thus the ease of handling is degraded. Accordingly, the volume of the communicating member 51 is preferably equal to or less than 1 $mm^3$, more preferably equal to or less than 0.5 $mm^3$, and most preferably equal to or less than 0.2 $mm^3$. Although the ideal volume of the communicating member 51 including the air inlet-and-outlet port 50 is 0 mm³. However, since a small volume also exists inside the pressure measurement means 60 for measuring a pressure, the volume cannot be 0 mm³.

(Liquid)

The liquid to be delivered in the pressure measurement unit 1 may be any body fluid or any drug solution and is not particularly limited. Examples of the body fluid may include, blood, plasma, lymph, tissue fluid, mucus, hormone, cytokine and urine, while examples of the drug solution may include physiological saline, anticoagulant agents, fresh frozen plasma, dialyzate solution, albumin solution, and replenisher for filtration artificial kidney.

Second Embodiment

Figure 6:
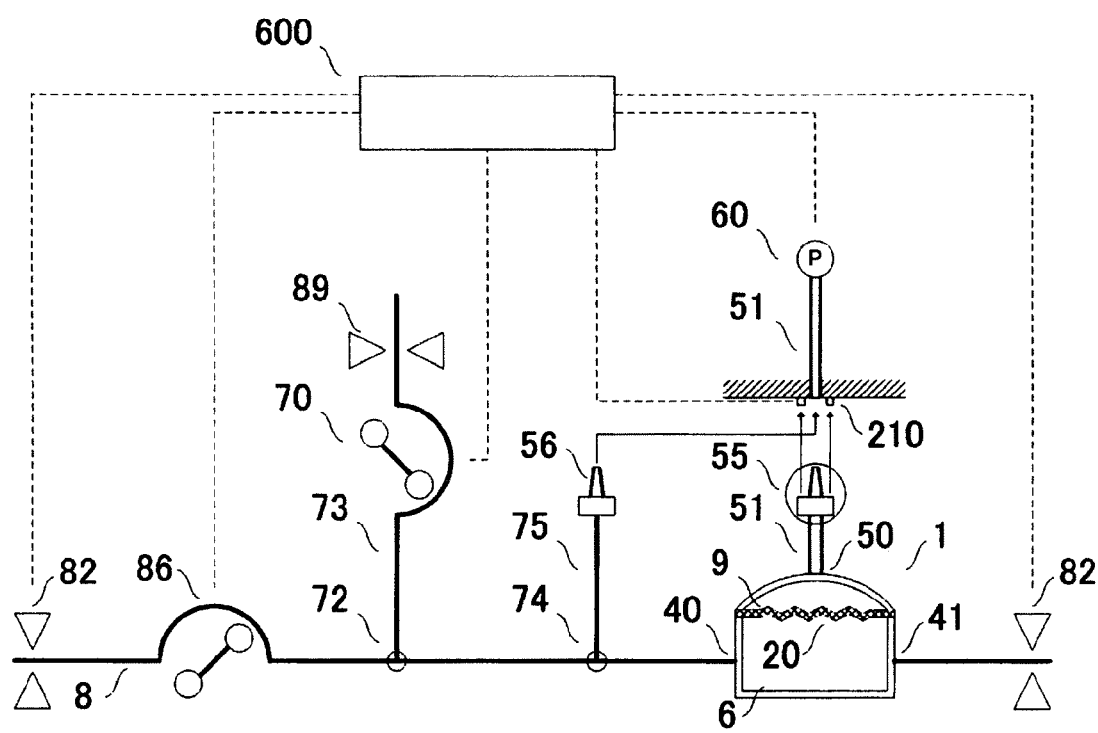
FIG. 6 is a schematic diagram showing a second embodiment for carrying out a method of calibrating a pressure measurement unit according to the present invention.

FIG. 6 is a schematic diagram showing a second embodiment for carrying out a method of calibrating a pressure measurement unit according to the present invention. Like components having substantially the same function as those in the first embodiment are indicated by like reference numerals, and the descriptions thereof will be omitted As shown in FIG. 6, the pressure measurement unit 1 includes: the air chamber 9 having the air inlet-and-outlet port 50, the liquid chamber 6 having the liquid inlet port 40 and the liquid outlet port 41, the flexible diaphragm 20 which is sandwiched between the air chamber 9 and the liquid chamber 6 to provide a partition between the air chamber 9 and the liquid chamber 6, the flexible diaphragm 20 deforming in accordance with a pressure difference between a pressure inside the air chamber 9 and a pressure inside the liquid chamber 6; and the pressure measurement means 60 which is connected to the air chamber 9 via a connection means 55, the pressure measurement means 60 measuring the pressure inside the liquid chamber 6 on the side of the air chamber 9 via the flexible diaphragm 20.

The second embodiment for carrying out the method of calibrating the pressure measurement unit according to the present invention includes: the pressure measurement unit 1 which is arranged in the extracorporeal circuit 8 sandwiched between two closing means 82; a first branch pipe 73 which is connected to a first branch point 72; the pressure adjusting pump 70 arranged in the first branch pipe 73; a second branch pipe 75 which is connected to a second branch point 74; and a second connection means 56 which is connected to the distal end of the second branch pipe 75 and which is connectable to a communicating member communicating with the first pressure measurement means 60.

The following description will describe in detail a method of calibrating the pressure measurement unit 1 which is carried out when the connection between the air inlet-and-outlet port 50 of the container on the air chamber 9 side and the first pressure measurement means 60 is disengaged at the first connection means 55 in the embodiment shown in FIG. 6 and it becomes impossible to continue pressure measurement.

First, the detection means 210 detects the disengagement of the pressure measurement unit 1 and transmits such information to the control means 600. The control means 600, upon the receipt of this information, stops the liquid sending means 86 and closes the extracorporeal circuit 8 using the two closing means 82.

Next, the first pressure measurement means 60 and the second branch pipe 75 are connected to each other via the second connection means 56 so that the pressure inside the extracorporeal circuit 8 can be monitored using the first pressure measurement means 60. Then the first pressure measurement means 60 measures a pressure $P_t$ of the closed section in the extracorporeal circuit 8 and transmits the information of the pressure $P_t$ to the control means 600, and the control means 600 controls, while monitoring the pressure using the first pressure measurement means 60, the pressure adjusting pump 70 so as to set the pressure inside the liquid chamber 6 to be a predetermined pressure $P_0$, thereby restoring the flexible diaphragm 20 to the position which allows for pressure measurement within a targeted pressure measurement range. Then by disengaging the connection between the first pressure measurement means 60 and the second branch pipe 75 connected via the second connection means 56 and by hermetically connecting the air inlet-and-outlet port 50 of the air chamber 9 and the first pressure measurement means 60 using the first connection means 55, it becomes possible to carry out stable pressure measurement again.

If the pressure inside the extracorporeal circuit 8 is lower than the initial pressure, the liquid inside the extracorporeal circuit 8 will flow into the second branch pipe 75 when the pressure is restored to the initial pressure. Accordingly, the volume of the second branch pipe 75 is suitably set so that, when the pressure inside the extracorporeal circuit 8 is restored from an expected pressure to the initial pressure, the liquid would not flow into the communicating member 51 of the first pressure measurement means 60.

Also, the second connection means 56 provided to the second branch pipe 75 needs to be a closed system when it is not connected to the first pressure measurement means 60. For example, a system using a coupler or a check valve is preferable since they are closed when not connected to the first pressure measurement means 60. Other connection means may be used in combination with a closing means for closing the second branch pipe 75, so the second connection means 56 does not have to be particularly limited. Examples of the closing means may include forceps, a manually-operated clamp and an electrically-operated valve. As examples of the electrically-operated valve, a rotary solenoid valve and a push-pull valve may be provided, but the closing means is not limited thereto and may employ any means which can close and open the second branch pipe 75.

With the configuration shown in FIG. 6, one of the expensive pressure measurement means can be eliminated, and therefore the second embodiment can achieve a lower cost than the first embodiment, and therefore it is effective for cost reduction.

Third Embodiment

Figure 7:
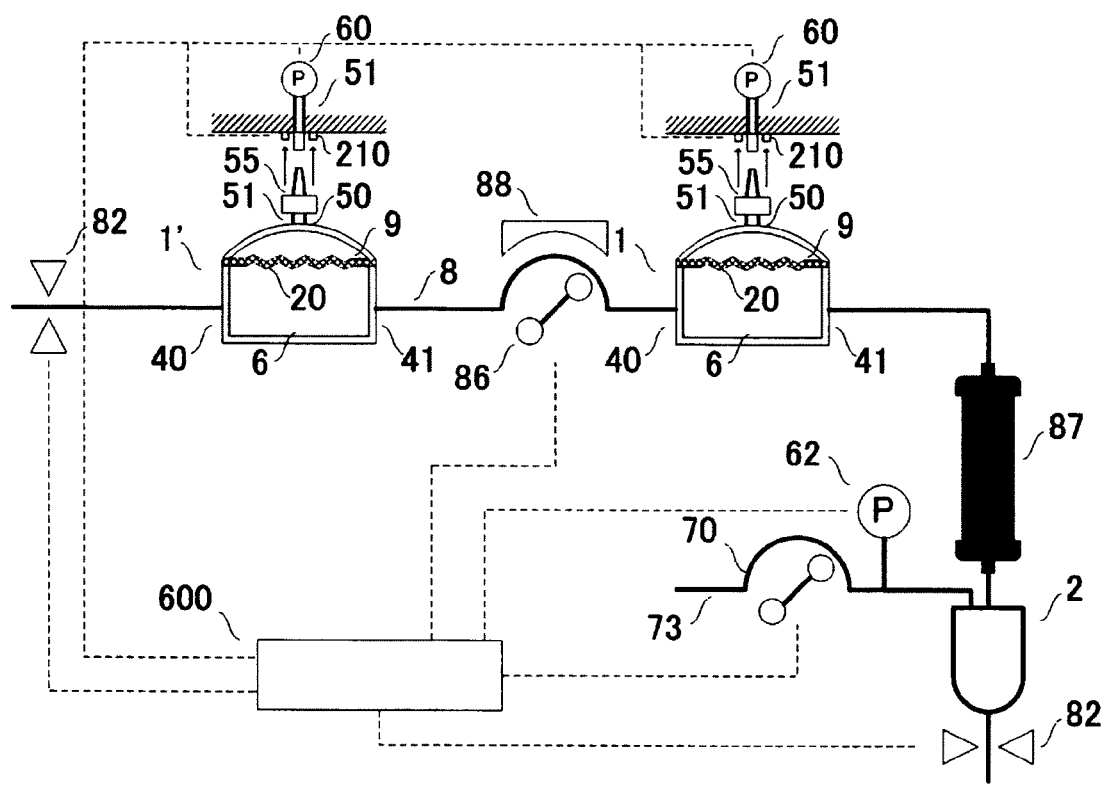
FIG. 7 is a schematic diagram showing a third embodiment for carrying out a method of calibrating a pressure measurement unit according to the present invention.
Figure 8:
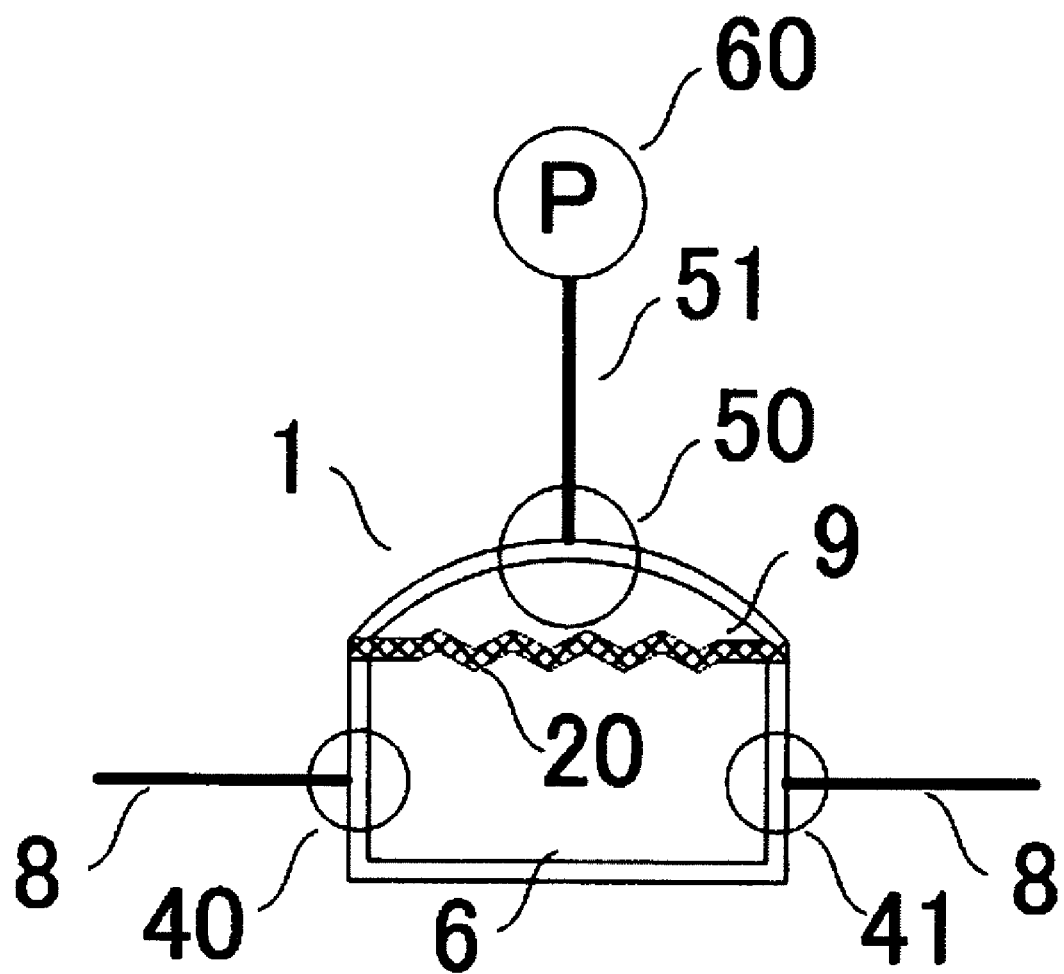
FIG. 8 is a schematic diagram showing a pressure measurement unit in the related art.
Figure 9:
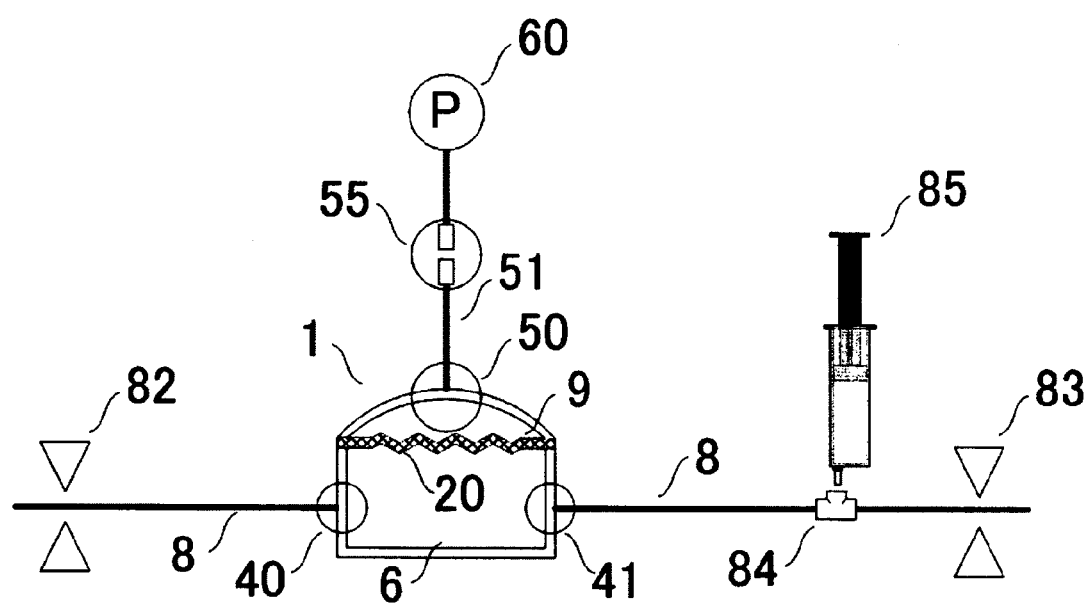
FIG. 9 is a schematic diagram explaining a method for carrying out a calibration for a pressure measurement unit in the related art.

FIG. 7 is a schematic diagram showing a third embodiment for carrying out a method of calibrating a pressure measurement unit according to the present invention. Like components having substantially the same function as those in the first and second embodiments are indicated by like reference numerals, and the descriptions thereof will be omitted In FIG. 7, the pressure measurement unit 1 and a pressure measurement unit 1', being pressure measurement means for the extracorporeal circuit 8, are arranged on the upstream and downstream of the liquid sending means 86, and the second pressure measurement means 62 for the extracorporeal circuit 8 is arranged on the downstream of a blood purifier 87 for purifying blood. In general, the second pressure measurement means 62 on the downstream of the blood purifier is connected via a drip chamber 2 which traps bubbles generated in the extracorporeal circuit 8. Furthermore, the pressure adjusting pump 70 for adjusting a liquid level in the drip chamber 2 is arranged in the branch pipe 73 branching from the drip chamber 2. In addition, the closing means 82 is arranged on the downstream of the drip chamber 2 so that, when a detection means (not shown) detects bubbles between the drip chamber 2 and the closing means 82, the closing means 82 blocks the extracorporeal circuit 8 in order to prevent the bubbles from being sent to the downstream of the closing means 82.

The blood purifier 87 is not particularly limited and may be selected so as to be suitable for a patient to whom it is to be applied, examples of which may include an artificial kidney used for the treatment of renal insufficiency, a continuous renal replacement therapy filter used for the treatment of acute renal insufficiency, as well as a plasma separator, a plasma component separator, a plasma component adsorber and an adsorption-type blood purifier used for the treatment of hepatic insufficiency.

If the pressure measurement unit 1, being the pressure measurement means for measuring the pressure inside the extracorporeal circuit 8, is provided only on the downstream of the liquid sending means 86, the configuration between the liquid sending means 86 and the closing means 82 is the same as the configuration shown in FIG. 2 in the first embodiment, and thus the method of calibrating the pressure measurement unit according to the present invention can be carried out.

However, if a tube pump as mentioned above is used as the liquid sending means 86 and the pressure measurement unit 1' for measuring the pressure inside the extracorporeal circuit is arranged on the upstream of the liquid sending means 86, the method as described in the first embodiment cannot be carried out.

Accordingly, as shown in FIG. 7, a liquid sending means having a movable housing 88 which can open or close the extracorporeal circuit 8 is employed as the liquid sending means 86 in the extracorporeal circuit 8, and the closing means 82 is arranged on the upstream of the pressure measurement unit 1'. In this configuration, by closing the extracorporeal circuit 8 with the two closing means 82 and then opening the extracorporeal circuit 8 which has been closed by the movable housing 88, it becomes possible to calibrate the pressure measurement unit in such a way that the pressures inside the liquid chambers 6 in the pressure measurement units 1 and 1' are restored to the initial pressure using the pressure adjusting pump 70 and the pressure measurement means 62 in the extracorporeal circuit 8.

INDUSTRIAL APPLICABILITY

The pressure measurement unit in the present invention is capable of, even when it is detached, being calibrated and then connected again, a pressure inside the extracorporeal circuit can be measured safely and accurately, and therefore the pressure measurement unit is useful in extracorporeal circulation therapy.

What is claimed is:

1. A method of calibrating a pressure measurement unit in an extracorporeal circuit system, the pressure measurement unit including a container having an air chamber provided with an air inlet-and-outlet port, a liquid chamber provided with a liquid inlet port and a liquid outlet port, and a flexible diaphragm that provides a partition between the air chamber and the liquid chamber and that deforms in accordance with a pressure difference between a pressure inside the air chamber and a pressure inside the liquid chamber;
  a first pressure measurer that is connected to the air inlet-and-outlet port of the container via a detachable connection;
  an upstream part and a downstream part of an extracorporeal circuit that are connected respectively to the liquid inlet port and the liquid outlet port of the liquid chamber;
  a closer that closes the upstream part and the downstream part of the extracorporeal circuit, respectively;
  second pressure measurer that measures pressure in an extracorporeal circuit part by the closer;
  a pressure adjusting pump provided in the extracorporeal circuit part closed by the closer or in a branch pipe branching from the extracorporeal circuit part; and
  a liquid sending pump provided in the extracorporeal circuit,
  the method being performed when a connection between the first pressure measurer and the air inlet-and-outlet port is disengaged after starting a pressure measurement for the extracorporeal circuit,
  the extracorporeal circuit system further including a detector and a controller, the method comprising:
  detecting, by the detector, the disengagement of the connection between the first pressure measurer and the air inlet-and-outlet port and transmitting information of the disengagement to the controller;
  stopping, by the controller, the liquid sending pump and closing the upstream part and the downstream part of the extracorporeal circuit using the closer;
  measuring, by the second pressure measurer, a pressure $P_t$ of the closed extracorporeal circuit part and transmitting information of the pressure $P_t$ to the controller;
  driving, by the controller, the pressure adjusting pump and setting the pressure $P_t$ to a predetermined pressure $P_0$, which is a pressure closer to the pressure at the time of starting the pressure measurement; and
  after the setting, connecting, the first pressure measurer and the air inlet-and-outlet port to each other again.

2. A method of calibrating a pressure measurement unit in an extracorporeal circuit system, the pressure measurement unit including a container having an air chamber provided with an air inlet-and-outlet port, a liquid chamber provided with a liquid inlet port and a liquid outlet port, and a flexible diaphragm that provides a partition between the air chamber and the liquid chamber and that deforms in accordance with a pressure difference between a pressure inside the air chamber and a pressure inside the liquid chamber;
  a pressure measurer that is connected to the air inlet-and-outlet port of the container via a detachable connection;
  an upstream part and a downstream part of an extracorporeal circuit connected respectively to the liquid inlet port and the liquid outlet port of the liquid chamber;
  a closer that closes the upstream part and the downstream part of the extracorporeal circuit, respectively;
  a pressure adjusting pump provided in an extracorporeal circuit part closed by the closer or in a branch pipe branching from the extracorporeal circuit part; and
  a liquid sending pump arranged in the extracorporeal circuit,
  the method being performed when a connection between the pressure measurer and the air inlet-and-outlet port is disengaged after starting a pressure measurement for the extracorporeal circuit,
  the pressure measurer is connectable to the closed extracorporeal circuit part; and
  the extracorporeal circuit system further comprising a detector and a controller, the method comprising:
  detecting, by the detector, the disengagement of the connection between the pressure measurer and the air inlet-and-outlet port and transmitting information of the disengagement to the controller;
  stopping, by the controller, the liquid sending pump and closing the upstream part and the downstream part of the extracorporeal circuit using the closer;

connecting the pressure measurer to the closed extracorporeal circuit part, measuring a pressure $P_t$ of the closed extracorporeal circuit part and transmitting information of the pressure $P_t$ to the controller;

driving, by the controller, the pressure adjusting pump and setting the pressure $P_t$ to a predetermined pressure $P_0$, which is a pressure closer to the pressure at the time of starting the pressure measurement; and after the setting, disengaging the connection between the pressure measurer and the closed extracorporeal circuit part, and connecting the pressure measurer and the air inlet-and-outlet port to each other again.

3. The method according to claim 1, further comprising automatically driving, by the controller, the pressure adjusting pump based on the information of the pressure $P_t$ and the pressure $P_0$, and setting the pressure $P_t$ to the pressure $P_0$.

4. The method according to claim 1, wherein:
the extracorporeal circuit system further includes a display and an input;
the controller displays information of the pressure $P_t$ and the pressure $P_0$, on the display;
the display instructs an operator to input information for setting the pressure $P_t$ to the pressure $P_0$ via the input; and
the controller drives the pressure adjusting pump based on the information input via the input so as to set the pressure $P_t$ to the pressure $P_0$.

5. The method according to claim 1, wherein:
the pressure adjusting pump is arranged in the branch pipe; and
a terminal end of the branch pipe is connected to a liquid supply source.

6. The method according to claim 1, wherein:
the pressure adjusting pump is arranged in the branch pipe; and
a terminal end of the branch pipe is open to the atmosphere.

7. The method according to claim 1, wherein:
the pressure adjusting pump is arranged in the branch pipe; and
the liquid sending pump has a movable housing which opens or closes the extracorporeal circuit, the liquid sending pump being positioned in the closed extracorporeal circuit part, the housing opening the extracorporeal circuit before the setting the pressure $P_t$ to the pressure $P_0$.

8. The method according to claim 1, wherein the pressure adjusting pump is provided in the extracorporeal circuit and integrated with the liquid sending pump and the closer.

9. The method according to claim 1, wherein two or more pressure measurement units are provided.

10. The method according to claim 2, further comprising automatically driving, by the controller, the pressure adjusting pump based on the information of the pressure $P_t$ and the pressure $P_0$, and setting the pressure $P_t$ to the pressure $P_0$.

11. The method according to claim 2, wherein:
the extracorporeal circuit system further includes a display and an input;
the controller displays information of the pressure $P_t$ and the pressure $P_0$, on the display;
the display instructs an operator to input information for setting the pressure $P_t$ to the pressure $P_0$ via the input; and
the controller drives the pressure adjusting pump based on the information input via the input so as to set the pressure $P_t$ to the pressure $P_0$.

12. The method according to claim 2, wherein:
the pressure adjusting pump is arranged in the branch pipe; and
a terminal end of the branch pipe is connected to a liquid supply source.

13. The method according to claim 2, wherein:
the pressure adjusting pump is arranged in the branch pipe; and
a terminal end of the branch pipe is open to the atmosphere.

14. The method according to claim 2, wherein:
the pressure adjusting pump is arranged in the branch pipe; and
the liquid sending pump has a movable housing which opens or closes the extracorporeal circuit, the liquid sending pump being positioned in the closed extracorporeal circuit part, the housing opening the extracorporeal circuit before the setting the pressure $P_t$ to the pressure $P_0$.

15. The method according to claim 2, wherein the pressure adjusting pump is provided in the extracorporeal circuit and integrated with the liquid sending pump and the closer.

16. The method according to claim 2, wherein two or more pressure measurement units are provided.

* * * * *